United States Patent
Zhang et al.

(10) Patent No.: US 10,507,104 B2
(45) Date of Patent: Dec. 17, 2019

(54) SUTURELESS VALVE PROSTHESIS DELIVERY DEVICE AND METHODS OF USE THEREOF

(71) Applicant: Suzhou Jiecheng Medical Technology Co., Ltd., WuJiang, Jiangsu (CN)

(72) Inventors: Ji Zhang, Burnaby (CA); Brandon G. Walsh, Syracuse, UT (US)

(73) Assignee: Suzhou Jiecheng Medical Technology Co., Ltd., Wujiang, Jiangsu (CN)

(*) Notice: Subject to any disclaimer, the term of this patent is extended or adjusted under 35 U.S.C. 154(b) by 276 days.

(21) Appl. No.: 14/774,037

(22) PCT Filed: Mar. 14, 2014

(86) PCT No.: PCT/US2014/029315
§ 371 (c)(1),
(2) Date: Sep. 9, 2015

(87) PCT Pub. No.: WO2014/153152
PCT Pub. Date: Sep. 25, 2014

(65) Prior Publication Data
US 2016/0015512 A1    Jan. 21, 2016

Related U.S. Application Data

(60) Provisional application No. 61/784,973, filed on Mar. 14, 2013.

(51) Int. Cl.
*A61F 2/06* (2013.01)
*A61F 2/24* (2006.01)

(52) U.S. Cl.
CPC .......... *A61F 2/2436* (2013.01); *A61F 2/2427* (2013.01)

(58) Field of Classification Search
CPC ........ A61F 2/2436; A61F 2/2427; A61F 2/95; A61F 2/962; A61F 2/966
USPC .............................. 606/108; 623/1.11, 2.11
See application file for complete search history.

(56) References Cited

U.S. PATENT DOCUMENTS

| | | | |
|---|---|---|---|
| 7,025,780 | B2 | 4/2006 | Gabbay |
| 7,387,640 | B2 | 6/2008 | Cummings |
| 7,510,572 | B2 | 3/2009 | Gabbay |
| 7,621,948 | B2 | 11/2009 | Herrmann et al. |
| 7,789,909 | B2 | 9/2010 | Andersen et al. |
| 7,803,185 | B2 | 9/2010 | Gabbay |
| 7,824,443 | B2 | 11/2010 | Salahieh et al. |
| 8,052,750 | B2 | 11/2011 | Tuval et al. |
| 8,105,375 | B2 | 1/2012 | Navia et al. |

(Continued)

FOREIGN PATENT DOCUMENTS

| | | |
|---|---|---|
| CN | 101919750 | 12/2010 |
| CN | 102036622 | 4/2011 |

(Continued)

OTHER PUBLICATIONS

International Search Report from PCT Patent Application No. PCT/US2014/029315 dated Jun. 25, 2014, application now published as International Publication No. WO2014/153152 on Sep. 24, 2014.

*Primary Examiner* — Melanie R Tyson
(74) *Attorney, Agent, or Firm* — Nathan S. Smith; Sujohn Das; Morgan, Lewis & Bockius LLP

(57) ABSTRACT

Devices and methods for delivering a sutureless valve (5) to repair a defective native valve are described herein. The devices and methods are particularly useful in minimally invasive procedures.

26 Claims, 9 Drawing Sheets

(56) References Cited

U.S. PATENT DOCUMENTS

| | | |
|---|---|---|
| 8,313,525 B2 | 11/2012 | Tuval et al. |
| 2002/0032481 A1 | 3/2002 | Gabbay |
| 2003/0036791 A1 | 2/2003 | Bonhoeffer et al. |
| 2003/0040792 A1 | 2/2003 | Gabbay |
| 2003/0149478 A1 | 8/2003 | Figulla et al. |
| 2004/0260394 A1 | 12/2004 | Douk et al. |
| 2005/0137688 A1 | 6/2005 | Salahieh et al. |
| 2005/0137689 A1 | 6/2005 | Salahieh et al. |
| 2005/0251251 A1 | 11/2005 | Cribier |
| 2006/0173524 A1 | 8/2006 | Salahieh et al. |
| 2006/0206192 A1 | 9/2006 | Tower et al. |
| 2006/0217802 A1 | 9/2006 | Ruiz et al. |
| 2006/0259135 A1 | 11/2006 | Navia et al. |
| 2007/0016286 A1 | 1/2007 | Herrmann et al. |
| 2007/0027533 A1 | 2/2007 | Douk |
| 2007/0100440 A1 | 5/2007 | Figulla et al. |
| 2007/0244552 A1* | 10/2007 | Salahieh ............... A61F 2/2418 623/2.11 |
| 2007/0250161 A1 | 10/2007 | Dolan |
| 2007/0260225 A1* | 11/2007 | Sakakine ........... A61M 25/0136 604/528 |
| 2008/0071361 A1 | 3/2008 | Tuval et al. |
| 2008/0071363 A1* | 3/2008 | Tuval .................... A61F 2/2418 623/2.1 |
| 2008/0082166 A1 | 4/2008 | Styrc et al. |
| 2008/0177381 A1 | 7/2008 | Navia et al. |
| 2009/0054968 A1 | 2/2009 | Bonhoeffer et al. |
| 2009/0054976 A1 | 2/2009 | Tuval et al. |
| 2009/0132035 A1 | 5/2009 | Roth et al. |
| 2009/0192585 A1 | 7/2009 | Bloom et al. |
| 2009/0216310 A1 | 8/2009 | Straubinger et al. |
| 2009/0240320 A1 | 9/2009 | Tuval et al. |
| 2009/0275934 A1* | 11/2009 | Baxter ............... A61B 18/1492 606/15 |
| 2009/0287299 A1 | 11/2009 | Tabor et al. |
| 2010/0249915 A1* | 9/2010 | Zhang .................. A61F 2/2418 623/2.11 |
| 2010/0274088 A1 | 10/2010 | West et al. |
| 2012/0172919 A1 | 7/2012 | Fifer et al. |

FOREIGN PATENT DOCUMENTS

| | | |
|---|---|---|
| CN | 102858273 | 1/2013 |
| WO | WO 2004/019825 | 3/2004 |
| WO | WO 2005/002466 A2 | 1/2005 |
| WO | WO 2009/155561 | 12/2009 |
| WO | WO 2010/121076 A2 | 10/2010 |
| WO | WO 2012/095455 A2 | 7/2012 |
| WO | WO 2014/153152 A1 | 9/2014 |

* cited by examiner

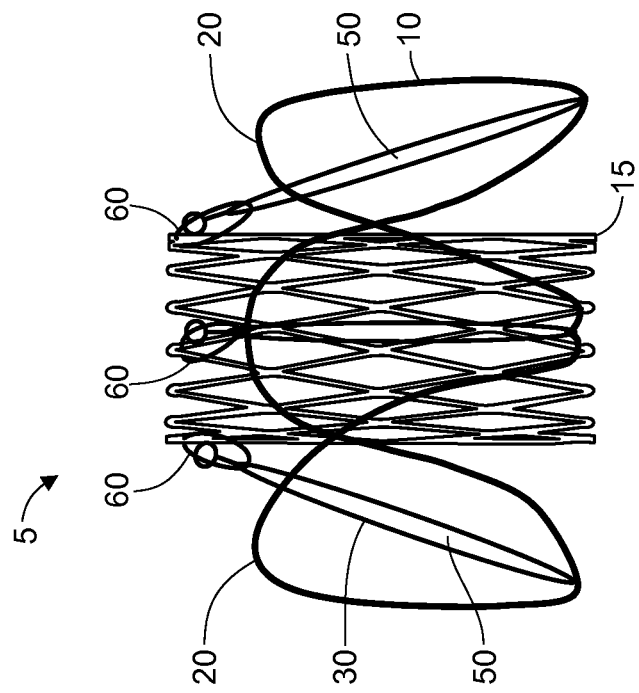
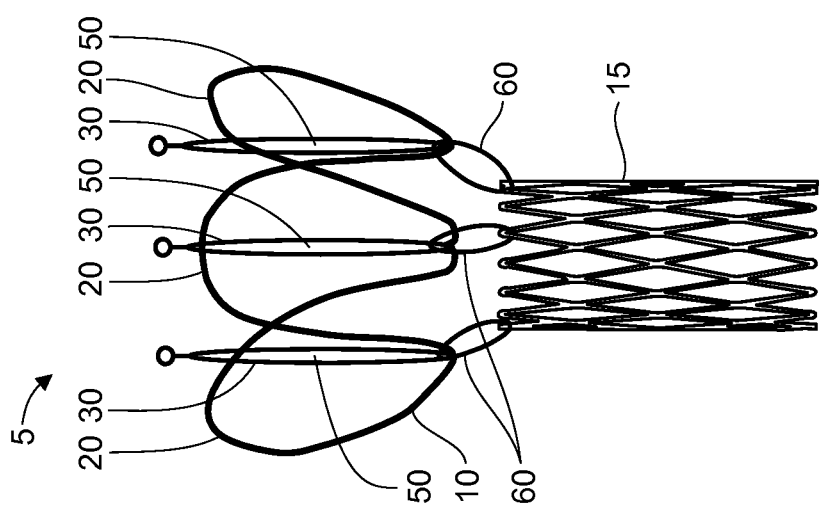

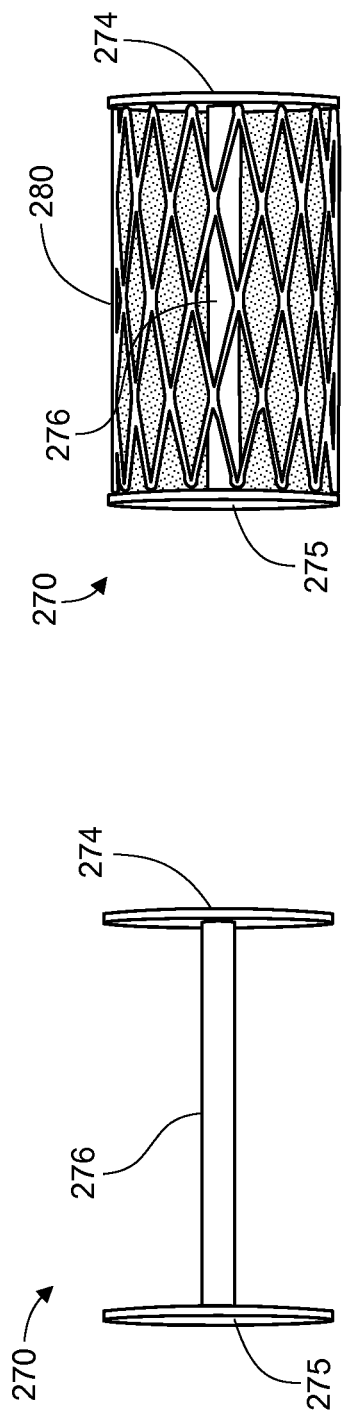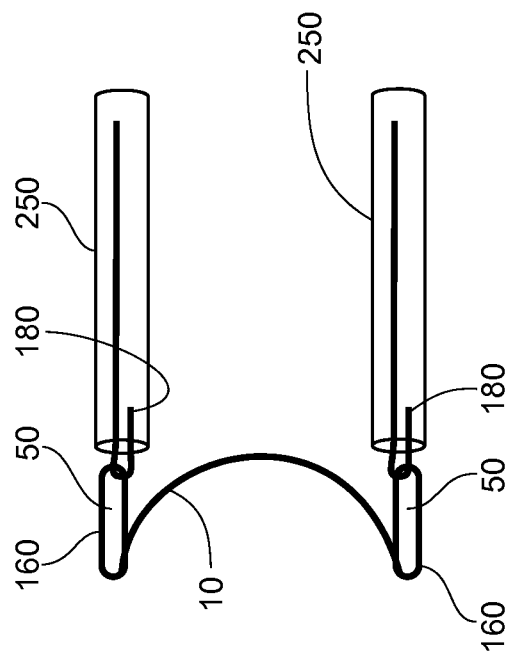

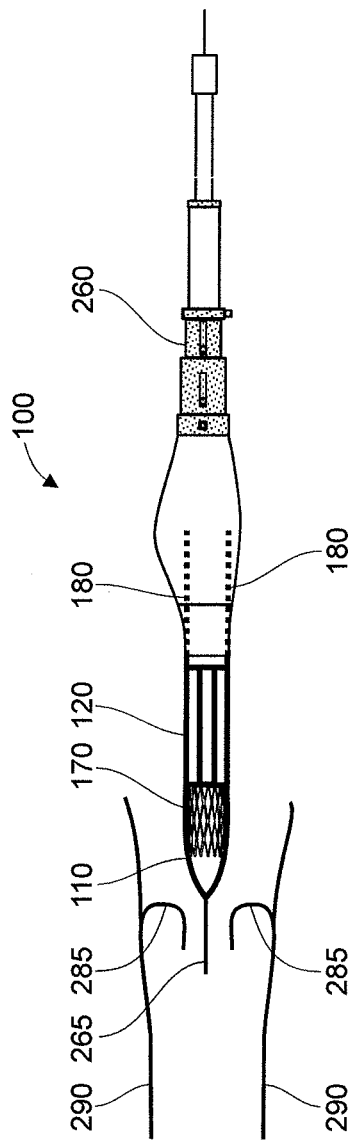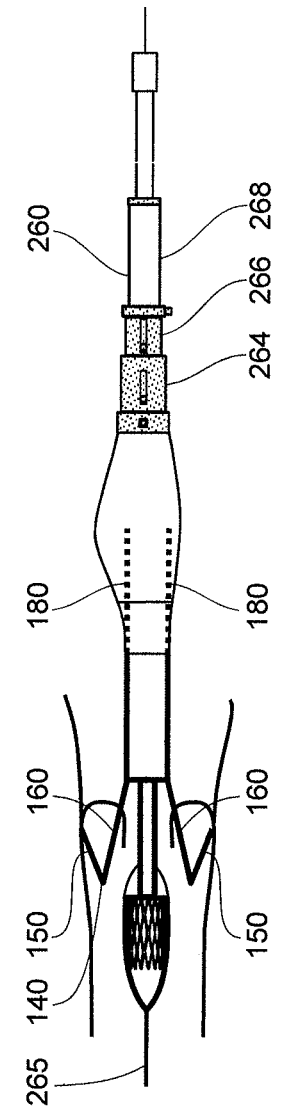

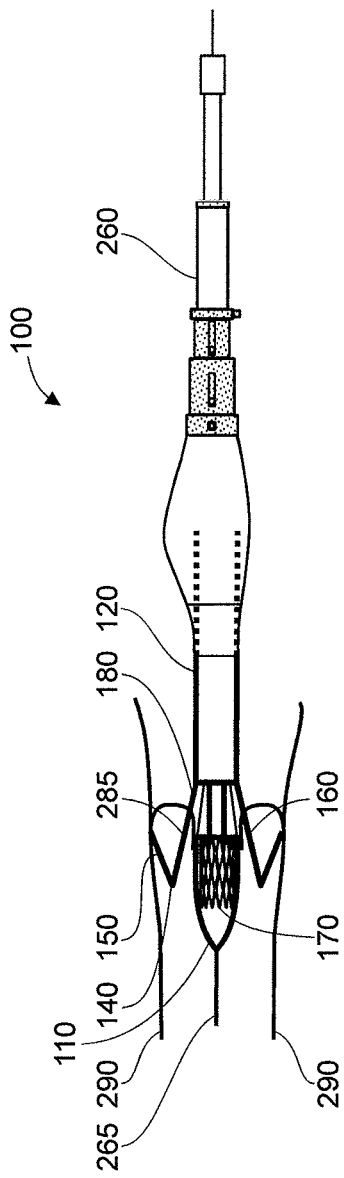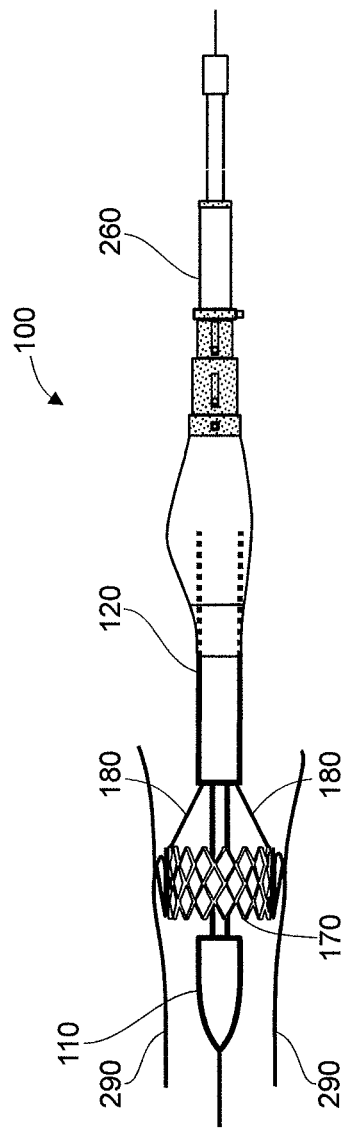

SUTURELESS VALVE PROSTHESIS DELIVERY DEVICE AND METHODS OF USE THEREOF

CROSS REFERENCE TO RELATED APPLICATIONS

This application is a U.S. National Stage of International Patent Application No. PCT/US2014/029315, filed Mar. 14, 2014, which claims the benefit of priority to U.S. Provisional Application No. 61/784,973, filed Mar. 14, 2013, the disclosures of which are all incorporated herein by reference in their entirety.

TECHNICAL FIELD

The subject matter described herein relates to medical devices and methods for the implantation of a sutureless prosthetic valve structure using minimally invasive procedures.

BACKGROUND

Prosthetic heart valves are used to replace damaged or diseased heart valves. In vertebrate animals, the heart is a muscular organ with four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Minimally invasive surgical techniques are evolving, where a valve prosthesis can be introduced into a patient using a catheter that is introduced via a small incision that provides access to, for example, a femoral artery or directly to the heart. These implantation techniques have shown promising results in providing treatment options for patients who are poor open surgical candidates. Nevertheless, challenges still remain in such catheter-based delivery of prosthetic valves. Advancing a tubular delivery device through a vessel exerts stress against the vessel walls and is carries the risk of damaging the vessel walls. For example, retrograde delivery of a valve through the femoral artery has been associated with aortofemoral artery injury/rupture, and carries a potential risk of stroke as the delivery involves crossing the aortic arch. Accordingly it is advantageous to design a valve prosthesis delivery system which minimizes damage along the delivery path of device while also minimizing the invasive nature of the implantation procedure.

In one embodiment described herein, a heart valve prosthesis delivery device allows implantation of an aortic valve prosthesis to correct a defective aortic valve. This device introduces the valve prosthesis through an introducer into the left ventricle of the heart (transapical delivery). In another embodiment disclosed here, a valve prosthesis delivery device is designed to take advantage of the relatively large diameter of the arteries and veins leading directly to the heart. This device is designed, for example, for use by a surgeon able to access these arteries and veins percutaneously such that introduction of the delivery device is done relatively close to the heart to take advantage of the larger diameter of the vessels.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, an implantation device comprised of a valve prosthesis and a delivery device is provided. The valve prosthesis comprises a valve clasper and a support frame radially expandable between a compact condition and an expanded condition, the support frame having an outer surface and defining a central orifice about an axis along an inflow-outflow direction. In one embodiment the support frame and valve clasper are movably connected. The delivery device comprises a control unit, an at least one track wire consisting of a proximal end attached to the control unit and a distal end for reversible connection with the valve clasper, a first sheath for encasing at least a portion of the support frame of the valve prosthesis in its compact condition, and a second sheath for encasing at least a portion of the valve clasper. In one embodiment, the delivery device is useful for apical delivery of an aortic valve prosthesis.

In one embodiment, the delivery device encases the valve prosthesis.

In one embodiment, the first sheath is distal to the second sheath and the second sheath is distal to the control unit along a longitudinal axis. In another embodiment, the delivery device comprises a central lumen along the longitudinal axis of the delivery device.

In one embodiment, the valve clasper is movable along the axis between a nesting position with the outer surface of the support frame and an engagement position.

In one embodiment, the valve clasper is comprised of a two, three, or four leg members and two, three, or four u-shaped members. In another embodiment, each u-shaped member comprises a straight portion and a curved portion. In still another embodiment, each of the leg members has a first and second end. In one embodiment, the first end of the leg member is the distal end of the leg member and the second end of the leg member is the proximal end of the leg member. In still another embodiment, the proximal end of each of the leg members has a hole.

In one embodiment, the valve clasper is comprised of a shape-memory material. In another embodiment, the valve clasper is fabricated as a single piece.

In one embodiment, the support frame has a length L, and each of the leg members are at least L in length. In another embodiment, the support frame has a length L, and each of the leg members are less than L in length. In yet another embodiment, the support frame has a length L, and each of the leg members are approximately L in length.

In another embodiment, the support frame in its expanded condition has a radius r, and the at least one valve clasper is dimensioned to concentrically nest with the support frame when the support frame is in its expanded condition.

In one embodiment, the support frame is comprised of a shape-memory material. In another embodiment, the support frame is at least partially covered by a covering. In certain embodiments, the covering is a fabric. In another embodiment, the support frame is balloon expandable.

In one embodiment, the support frame comprises a plurality of flexible leaflets attached to the support frame to provide a one-way valve in the orifice when the support frame is in its expanded condition. In another embodiment, the plurality of flexible leaflets is comprised of a biological material. In certain embodiments, the biological material is porcine or bovine.

In one embodiment, the delivery device further comprises a valve carrier. In another embodiment, the valve carrier comprises a distal disc portion, a central stem portion and a proximal disc portion. In another embodiment, the valve carrier is fully encased by the first sheath. In one embodiment, the valve carrier comprises a balloon which can be inflated to effect radial expansion of the support frame.

In one embodiment, the support frame is fully encased by the first sheath. In another embodiment, the support frame fully encased by the first sheath is in a position between the distal disc portion and the proximal disc portion of the valve carrier.

In one embodiment, the valve clasper is at least partially encased by the second sheath. In another embodiment, the u-shaped members are partially or fully encased by the second sheath. In still another embodiment, the distal end of the valve clasper is fully encased by the first sheath.

In one embodiment, the first or second sheath is comprised of a material which can bend, wherein the sheath can bend to a bended configuration, wherein the bend has an angle ranging from about 5 degrees to 60 degrees, 10 degrees to 60 degrees, 10 degrees to 50 degrees, 20 degrees to 40 degrees, 30 degrees to 50 degrees, 10 degrees to 40 degrees, 10 degrees to 30 degrees, 5 degrees to 20 degrees, 10 degrees to 20 degrees, 15 degrees to 30 degrees, 40 degrees to 60 degrees, 50 degrees to 60 degrees, or 30 degrees to 60 degrees. In another embodiment, the first or second sheath will maintain the bended configuration during delivery of the valve prosthesis and removal of the delivery device.

In one embodiment, the first or second sheath comprises a metal support structure and a protective layer. In another embodiment, the metal support structure is tubular in shape. In yet another embodiment, the metal support structure comprises a metal wire mesh. In still another embodiment, the metal support structure is fabricated from one or more thin-walled, flat-wire, metal helical coils. In one embodiment, the first or second sheath is comprised of a both a metal and a polymer which are fabricated together to form a long tube which can be bent to a bent configuration and which can maintain the bent configuration during a portion of or the entire delivery procedure.

In one embodiment, the wall of the first or second sheath has a thickness of 0.04 mm to 1.0 mm, 0.05 mm to 0.7 mm, 0.05 mm to 0.1 mm, 0.05 mm to 0.3 mm or 0.04 mm to 0.6 mm.

In one embodiment, the first or second sheath comprises a polymer material. In yet another embodiment, the polymer material is Pebax, Teflon, or similar polymer. In another embodiment, the polymer is a polyether-based polyamide. In still another embodiment, the polymer material is Pebax, Teflon, or another similar polymer.

In one embodiment, the polymer material of the first or second sheath is a protective covering which covers the metal support structure. In another embodiment, the protective covering is present on the outer surface of the tubular metal support structure. In still another embodiment, the protective covering is present on the luminal surface of the tubular metal support structure.

In one embodiment, the first or second sheath comprises a metal support structure embedded in or impregnated with the polymer material.

In one embodiment, the number of track wires is equal to the number of leg members. In still another embodiment, the distal end of each track wire is threaded through a hole in the proximal end of a leg member. In yet another embodiment, the proximal end of each clasper connector cable is in operable contact with the control unit.

In one aspect, a method for delivering the sutureless valve prosthesis is provided, wherein the delivery device comprises a first sheath, a second sheath, and a control unit for delivery of the sutureless valve prosthesis as described above.

In one embodiment, the method comprises introducing the delivery device into the left ventricle of the heart of a subject through an introducer.

In one embodiment, the method further comprises advancing a distal portion of the delivery device through the left ventricle in the direction of blood flow until the first sheath is located distal to the native aortic valve.

In one embodiment, the method further comprises moving the second sheath in a proximal direction to uncover the valve clasper. In this embodiment, the first sheath with encased support frame, the valve clasper, and the control unit can be held stationary. In another embodiment, the u-shaped members of the valve clasper extend radially after the u-shaped members are uncovered.

In one embodiment, the method further comprising moving the delivery device in a proximal direction until the u-shaped members of the valve clasper are in contact with the sinus of the native valve between the native valve leaflet and the vessel wall. In this embodiment, the method further comprises moving the first sheath with encased support frame in a proximal direction to align the support frame with the valve clasper. In one embodiment, the proximal end of the support frame is approximately aligned with the proximal end of the u-shaped members.

In an alternative embodiment, after the valve clasper is uncovered, the first sheath with the encased support frame is moved in a proximal direction while the valve claspers are held stationary along the longitudinal axis, until the support frame is aligned with the valve clasper. In one embodiment, the first sheath is moved in a proximal direction until the proximal end of the support frame is approximately aligned with the proximal end of the u-shaped members. In one embodiment, the method further comprises moving the delivery device in a proximal direction until the u-shaped members of the valve clasper are in contact with the sinus of the native valve between the native valve leaflet and the vessel wall.

In one embodiment, the method further comprises advancing the first sheath in a distal direction while holding the support frame stationary along the longitudinal axis.

In one embodiment, the method further comprises disconnecting the distal end of each of the track wires from the proximal end of each of the leg members of the valve clasper.

In one embodiment, the method further comprises moving the second sheath in a distal direction until the distal end of the distal sheath is approximately adjacent to and/or in contact with the proximal end of the first sheath.

In one embodiment, the method further comprises moving the delivery device in a proximal direction to remove the delivery device from the subject.

In one aspect, a sutureless valve prosthesis delivery device for antegrade delivery of a sutureless valve is provided.

In one aspect, an implantation device is provided which comprises a delivery device and a valve prosthesis. In one embodiment, the delivery device comprises a first sheath, a second sheath, and a control unit. In another embodiment, the first sheath is distal to the second sheath and the second sheath is distal to the control unit. In another embodiment, the delivery device comprises a central lumen along the longitudinal axis of the delivery device.

The valve prosthesis comprises a valve clasper and a support frame radially expandable between a compact condition and an expanded condition, the support frame having an outer surface and defining a central orifice about an axis along an inflow-outflow direction. The valve clasper has a circular axis with a central lumen and comprises two, three, or four leg members and two, three, or four u-shaped members. In one embodiment, the valve clasper and support frame are movably connected.

In one embodiment, an apex member is present between two u-shaped members. In another embodiment, the apex member is positioned between and connected to 1 u-shaped member and 1 leg member. In another embodiment the clasper unit is fabricated from 3 individual u-shaped members and 3 individual leg members. In another embodiment, the clasper unit is comprised of a shape-memory material.

In one embodiment, the valve prosthesis comprises at least one suture loop in contact with the support frame and with the valve clasper. In another embodiment, each of the at least one suture loop is moveably attached to the valve clasper. In still another embodiment, each of the at least one suture loop is attached to one of the leg members of the valve clasper. In another embodiment, the suture loop is able to slide along the leg member along the longitudinal axis of the leg member. In yet another embodiment, the suture loop is fixed to the support frame and movably attached to the leg member.

In one embodiment, the valve prosthesis comprises a plurality of flexible leaflets attached to the support frame to provide a one-way valve in the orifice when the support frame is in its expanded condition and the valve clasper movable along the axis between a nesting position with the outer surface of the support frame and an engagement position. In one embodiment, the support frame is comprised of a shape-memory material.

In one embodiment, the support frame has a length L, and each of the straight portions of the u-shaped member is at least L in length. In another embodiment, the support frame has a length L, and each of the straight portions of the u-shaped member is less than L in length. In yet another embodiment, the support frame has a length L and each of the straight portions of the u-shaped member is approximately L in length. In still another embodiment, the support frame is at least partially covered by a covering. In certain embodiments, the covering is a fabric. In one embodiment, the support frame is not self-expanding, and may be expanded, for example, using a balloon catheter as is well known in the art.

In one embodiment, the delivery device comprises a control unit, a first sheath for encasing a distal portion of the valve clasper leg members, and a second sheath for encasing the support frame of the valve prosthesis in its compact condition and at least the u-shaped members of the valve clasper in the compact condition.

In one embodiment, the delivery device comprises a locking member which is at least partially encased by the first sheath. In another embodiment, at least a portion of the distal end of each of the leg members is positioned between the locking member and the internal wall of the first sheath. In still another embodiment, the locking member is disc-shaped. In another embodiment, when the distal portion of the clasper is positioned between the outer surface of the locking member and the inner surface of the first sheath, the locking member functions to hold the clasper stationary while the second sheath is moved in a proximal direction along the longitudinal axis.

In one embodiment, the valve prosthesis is an aortic valve prosthesis, a pulmonary valve prosthesis, a mitral valve prosthesis, or tricuspid valve prosthesis.

In one embodiment, the second sheath is comprised of a flexible material. In another embodiment, the second sheath comprises a metal support structure which is a braid of metal wires, a wire mesh and/or a wire coil. In another embodiment, the second sheath is able to bend sufficiently to conform to the curve of the vessel through which the delivery device is advanced. The wire support structure of the second sheath is fabricated such that the second sheath can be bent to a particular angle prior to introduction of the delivery device into a patient. Once bent, the second sheath maintains the bent angle throughout delivery of the prosthetic valve and retrieval of the delivery device. The bent angle can match or be compatible with delivery of the prosthetic valve to the native valve annulus, such that delivery does not result in damage to the native tissue near the point of valve replacement, or decreases damage relative to damage which might be caused if the second sheath were straight or bent with an angle less that about 5 degrees or less than about 3 degrees.

The second sheath may also comprise a polymer material or other suitable material which may cover the metal support structure described above. Alternatively, the metal support structure is embedded in or impregnated with the polymer material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-£-isobutylene-£-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In alternative embodiments, the first sheath may be comprised of a metal support structure and/or a polymer as described for the second sheath.

In another aspect, a method of delivering a sutureless valve prosthesis using a retrograde approach is provided, comprising use of an implantation device which comprises a delivery device as described above, wherein the implantation device comprises a control unit, a delivery device, and a prosthetic valve, and wherein a support frame and valve clasper are encased in a second sheath. This device useful for percutaneous delivery of a valve prosthesis via a vessel leading to the heart, wherein the vesicle was accessed via surgical means. For example, this device can deliver a valve prosthesis to replace a native pulmonary or atrial valve through retrograde delivery of the prosthetic device.

In one embodiment, the method comprises inserting the distal end of the delivery device into a vessel of a patient by inserting the device into an incision made in the vessel. The device is then advanced in a direction that is opposite of blood flow to a valve annulus. In one embodiment, the delivery device is advanced until the first sheath is about in the annulus of the valve to be repaired. The second sheath is then moved in a proximal direction until the u-shaped members of the valve clasper can expand radially from the longitudinal axis of the delivery device. In one embodiment, the first sheath and the valve clasper is held stationary when the second sheath is moved in the proximal direction.

In one embodiment, the method then comprises moving the second sheath in a distal direction while the first sheath and valve clasper are held stationary along the longitudinal axis.

In one embodiment, the method then comprises moving the second sheath in a distal direction until the support frame is aligned with the valve clasper.

In one embodiment, the method then comprises moving the delivery device in a distal direction until the u-shaped members of the valve clasper are in contact with the sinus of the native valve between the native valve leaflet and the vessel wall.

In one embodiment, the method then comprises moving the second sheath in a proximal direction while holding the support frame stationary along the longitudinal axis until the support frame expands in a radial direction and contacts the native valve leaflets, wherein the u-shaped members of the valve clasper are located between the vessel wall and the native leaflet and the native leaflet is located between the u-shaped member and the outer surface of the support frame.

In one embodiment, the method then comprises moving the delivery device in a proximal direction. In another embodiment, the delivery device is removed from the patient.

In one embodiment, the method comprises imaging the location of the native valve to be replaced prior to inserting the delivery device into the patient. In another embodiment, the second sheath of the delivery device is bent to form a bent conformation which has an angle compatible with the angle of the native valve structure. In still another embodiment, the second sheath of the delivery device is bent to form the bent conformation or configuration prior to or during delivery of the valve prosthesis.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIGS. 1 and 2 illustrate an embodiment of a valve clasper movably connected to a support frame.

FIGS. 3A and 3B illustrate an embodiment of a valve carrier without and with a support frame, respectively.

FIG. 3C illustrates an embodiment of a track wire reversibly connected to leg members of a valve clasper.

FIGS. 4-7 illustrate embodiments of a delivery device for antegrade delivery of a sutureless valve prosthesis.

DETAILED DESCRIPTION

Figure 8:
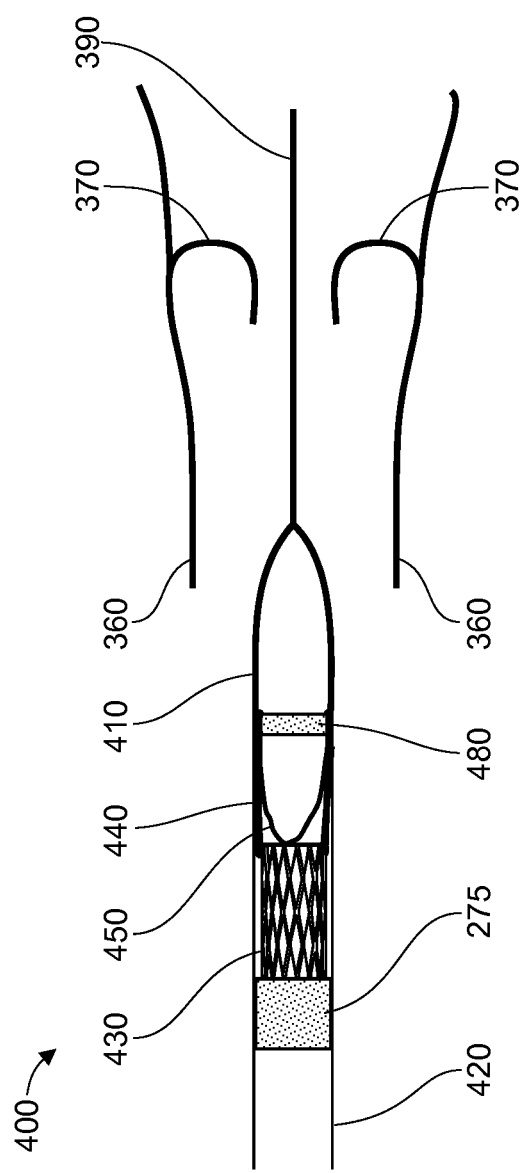
FIGS. 8-10 illustrate embodiments of a delivery device for retrograde delivery of a sutureless valve prosthesis.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Valve Claspers and Support Frame

The implantation devices described herein comprise a delivery device which is configured to deliver a valve prosthesis to a defective heart valve in a patient. The valve prosthesis comprises the valve clasper which is moveably connected to a radially-expandable support frame comprising prosthetic valve leaflets. Valve claspers as described herein are movable relative to and along the longitudinal axis of the support frame. When the valve clasper is off-set from the support frame, e.g., when the u-shaped member of the valve clasper is in a position proximal or distal to the support frame and/or does not approximately fully overlap with the support frame, this position is referred to as the engagement position. In this position, the u-shaped members of a valve clasper may extend radially from a leg member and the longitudinal axis of support frame which is in its compact condition. The u-shaped members can also move proximally or distally along the longitudinal axis when the support frame is held stationary in a compact condition. When the valve clasper is in the nesting position, the clasper apex is approximately adjacent to the end of the support frame which is aligned with the floor of a native valve sinus. Alternatively, the valve clasper is in its nesting position when at least a portion of the u-shaped member is in contact or adjacent to the floor of a native sinus or the commissures of the native leaflets of the valve. A sutureless valve is further described for example, in U.S. Pat. No. 8,366,768, the contents of which are incorporated herein by reference in their entirety.

The valve clasper has a circular axis and is comprised of two, three or four u-shaped members which are separated by leg members. In some embodiments, each leg member comprises a lumen along the longitudinal axis of the leg member. This lumen allows attachment of, for example, a suture loop or other means that can move along the longitudinal axis of the leg member while remaining connected to the leg member. Accordingly, the suture loop can slide along the lumen. In the described valve prostheses, the suture is also attached to the support frame. The attachment to the support frame may either be immobile or have limited mobility with respect to support frame. This configuration in which a suture loop is attached to both the support frame and to the lumen of the valve clasper leg member allows the support frame and the valve clasper to be movably attached.

The valve clasper is movably connected (alternatively, "movably attached") to the support frame such that the valve clasper may be moved from a proximal or distal position from the support frame to a concentric position with the support frame. During delivery of the valve prosthesis, it is advantageous to have the valve clasper positioned serially from the support frame. This allows the user to minimize the radius of the device which must be advanced through, for example, arteries and veins. The distance from which the valve clasper may be serially displaced from the support frame is highly variable, such that the valve clasper may be adjacent to the support frame, or potentially inches or feet away from the support frame during the delivery procedure. In some embodiments, no part of the valve clasper is physically fixed to the support frame, such as by welding or otherwise adhering. Importantly, portions of the valve clasper can move radially from the support frame. Regardless, the valve claspers remain movably connected to the support frame. A skilled artisan will understand that the means for movably connecting the support frame and claspers is not limited to a suture loop as shown in FIGS. 1 and 2.

An example of a valve clasper movably attached to a support frame is illustrated in FIGS. 1 and 2. Valve clasper movably attached to a support frame 5 comprises a valve clasper 10, an expandable support frame 15 and suture loops 60. Valve clasper 10 comprises three leg members 30, each of which have a lumen 50 along which suture loop 60 can slide along the longitudinal axis. FIG. 1 represents an "engagement position" as described herein. FIG. 2 illustrates an embodiment in which support frame 15 is aligned with valve clasper 10, as would be the case when valve clasper 10 and support frame 15 are properly positioned within the native valve annulus (described herein as a "nesting position"), prior to deployment of support frame 15.

Prior to delivery of a valve prosthesis to a defective native valve annulus, the valve clasper and support frame are located adjacent to one another along a longitudinal axis with little or no overlap between the two (see, for example, FIG. 1). Also, both are in a compact condition within a first and/or second cylindrical sheath or tube. During implantation of the valve prosthesis, the support frame can be concentric with and interior to the valve clasper (see, for example, FIG. 2). After deployment of the support frame, each native valve leaflet will be positioned between a leg member and the expanded support frame. This configuration in combination with the radial force of the support frame secures the valve prosthesis within the native valve annulus.

The support frame has an outer or external surface and defines a central orifice about an axis (the longitudinal axis). The longitudinal axis corresponds to the inflow-outflow axis. In some embodiments, the valve prosthesis further comprises a plurality of prosthetic valve leaflets which are attached to the inner surface of the support frame. The valve leaflets have surfaces defining a reversibly sealable opening for unidirectional flow of a liquid through the prosthetic valve. The prosthetic valve can include three valve leaflets for a tri-leaflet configuration. As appreciated, mono-leaflet, bi-leaflet, and/or multi-leaflet configurations are also possible. For example, the valve leaflets can be coupled to the valve frame so as to span and control fluid flow through the lumen of the prosthetic valve. The prosthetic leaflets comprise synthetic material, engineered biological tissue, biological valvular leaflet tissue, pericardial tissue, cross-linked pericardial tissue, or combinations thereof. In other embodiments, the pericardial tissue is selected from but not limited to the group consisting of bovine, equine, porcine, ovine, human tissue, or combinations thereof.

The support frame can be self-expanding or balloon-expandable. In some embodiments, the self-expanding support frame can be comprised of a shape-memory metal which can change shape at a designated temperature or temperature range. Alternatively, the self-expanding frames can include those having a spring-bias. The material from which the support frame is fabricated allows the support frame to automatically expand to its functional size and shape when deployed but also allows the support frame to be radially compressed to a smaller profile for delivery through the patient's vasculature. Examples of suitable materials for self-expanding component as described herein (e.g., support frames, valve claspers, locking members) include, but are not limited to, medical grade stainless steel, titanium, tantalum, platinum alloys, niobium alloys, cobalt alloys, alginate, or combinations thereof. Examples of shape-memory materials include shape memory plastics, polymers, and thermoplastic materials which are inert in the body. Shape memory alloys having superelastic properties generally made from ratios of nickel and titanium, commonly known as Nitinol, are preferred materials. In an alternative embodiment, the support frame is not self-expanding, and may be expanded, for example, using a balloon catheter as is well known in the art.

Prior to deployment of the support frame, the support frame can be held stationary within the first sheath by using a valve carrier. A valve carrier is illustrated in FIG. 3A (without a support frame) and FIG. 3B (with a support frame). A proximal disc member 275 and a distal disc member 274 of valve carrier 270 have a circumference which allows each end to push radially against the wall of the first sheath. A support frame 280 shown in FIG. 3B is situated between proximal disc member 275 and distal disc member 274. A central stem runs longitudinally between the proximal and distal ends of the valve carrier. In one embodiment, the central stem may comprise a balloon which can be inflated after displacing the support frame from the first sheath to provide deployment of the support frame. Such an embodiment may be used if the support frame is not made of a shape memory metal.

II. A Valve Prosthesis Delivery Device for Delivery of an Aortic Valve Prosthesis The present disclosure describes a delivery device which can provide, for example, transapical delivery of a sutureless valve prosthesis through the apex of the left ventricle of a mammalian heart. Such methods include the use of a trocar to provide a path of delivery through the chest of a patient. The device described below is not, however, limited to repair of an aortic valve.

An "antegrade" delivery device refers to a device which is delivered into the patient, through a vessel (vein or artery) or blood chamber (for example ventricle or atrium) in the direction of the blood flow through that vessel or chamber.

A "retrograde" delivery device refers to a device which is delivered into the patient, through a vessel (vein or artery) in the direction opposite that of the blood flow through that vessel.

The implantation device comprising a delivery valve and valve prosthesis is illustrated in FIGS. 4-7 and is described below.

It is envisioned that this device and variants of it may be used for the antegrade delivery of the valve prosthesis. In other words, this device and methods are useful for delivering and implementing the valve prosthesis wherein the distal end of the device (nose cone) is advance toward the native valve annulus in the direction of the blood flow. This delivery device can be used for repair of an aortic, mitral, pulmonary or tricuspid valve. One might also envision use of this device and methods for treatment of valves elsewhere in the circulatory system.

A sutureless valve prosthesis as described here comprises a valve clasper, such as a valve clasper 10 which is illustrated in FIGS. 1 and 2. Valve claspers may alternatively be referred to as sinus locators, valve positioners, or valve hangers. FIGS. 1 and 2 show an exemplary embodiment in which a suture loop 60 is threaded through a lumen 50 within a clasper leg member 30 to form a valve prosthesis in which the clasper is movably attached to the support frame. Each of the valve claspers can be connected to the support frame of the valve prosthesis by suture, fabric and/or flexible member, or other equivalent mechanism or structure.

The sutureless valve prosthesis is delivered to a defective native valve using, for example, apical delivery in which a delivery device housing the valve prosthesis is introduced into the left ventricle of the heart via an introducer which has pierced the chest wall. An exemplary delivery device 100 is illustrated in FIG. 4.

At the distal end of delivery device 100 is a first sheath 110 (alternatively, a nose cone) which encases a support frame 170 in a compact condition. A valve clasper 140 (shown in FIG. 5 in an expanded condition) is encased in a second sheath 120 and is movably connected to support frame 170 prior to delivery and deployment of the valve prosthesis. As shown in FIG. 6, u-shaped members 150 of valve clasper 140 will eventually be positioned between a native valve leaflet 285 and a vessel wall 290. Delivery device 100 also comprises at least one track wire 180 which forms a temporary connection at its distal end to the proximal end of a leg member 160 of valve clasper 140. There is one track wire for each leg member of the valve clasper. Track wires 180 forms an operable connection between leg members 160 and control unit 260. Control unit 260 can be comprised of multiple parts which act independent of one another or which act in combination with each other. For example, control unit 260 can comprise individual units which include but are not limited to a nose cone control unit, a sheath control unit, a release unit, and a handle. A handle can be the portion of the control unit which provides a place for the practitioner to hold delivery device 100 and does not necessarily have any other function (see, for example, a handle portion 266 in FIGS. 4 and 5). It is understood that any of the delivery devices described herein comprises a control unit for controlling various components of the delivery device. Such a control unit is one which is understood by the person having ordinary skill in the art. The control unit is made up of independent control elements which may be arranged in any manner which allows their manipulation to control various components of the delivery device, either independently of one another or in concert with one another. Independent control units may, for example, contain a lever, knob, or other similar structure for controlling movement of the first sheath, the second sheath, the valve prosthesis, each or all of the valve claspers, and each or all of the track wires. In one embodiment, one or more of the independent control elements appears as a section of a control unit 260 which can be rotated independently such as 264, 266, and 268, in FIGS. 4-5. Each of these independent control elements can be ordered in any manner. In one embodiment, the handle portion remains stationary relative to movement of the independent control elements.

Second sheath 120 can be comprised of a material which can be bent to allow second sheath 120 to maintain a bent configuration which will conform to the natural curvature of the heart and associated vessels near the location of the defective valve to be replaced. Prior to performing the implantation procedure, imaging of the patient is performed in the area of the defective valve. The imaging can be performed, for example, by ultrasound, X-ray, and/or magnetic resonance imaging (MRI). Such imaging allows the practitioner to bend second sheath 120 to an angle that is approximately the angle of curvature seen by the imaging. Bending second sheath 120 can prevent or reduce problematic contact between delivery device 100 and the luminal surface of the vessel or interior surface of the heart chamber, such as contact which may cause puncturing of a vessel or damage to heart tissue. A compatible bent configuration as intended herein is the angle which allows delivery of the valve prosthesis using device 100 without causing damage to any vessels or heart tissue during the delivery procedure. Alternatively, a compatible bent configuration is an angle which reduces damage to any vessels or heart tissue during the delivery procedure as compared to damage which may occur if second sheath 120 were rigid or if second sheath 120 was unable to maintain a straight or bent configuration (such as soft tubing).

Figure 11:
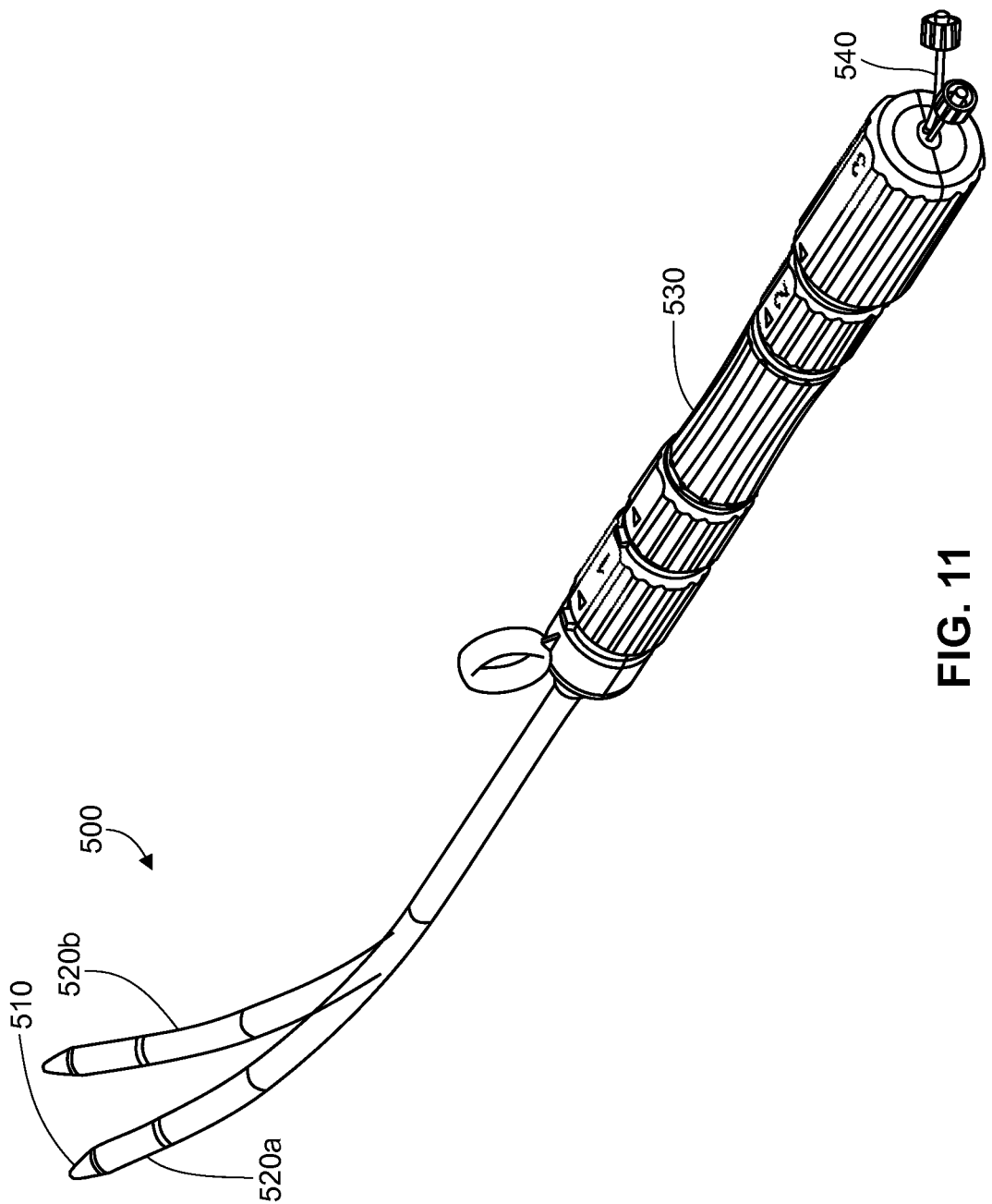
FIGS. 11-12 illustrate embodiments of a flexible sheath for delivery of a sutureless valve prosthesis.
Figure 12:
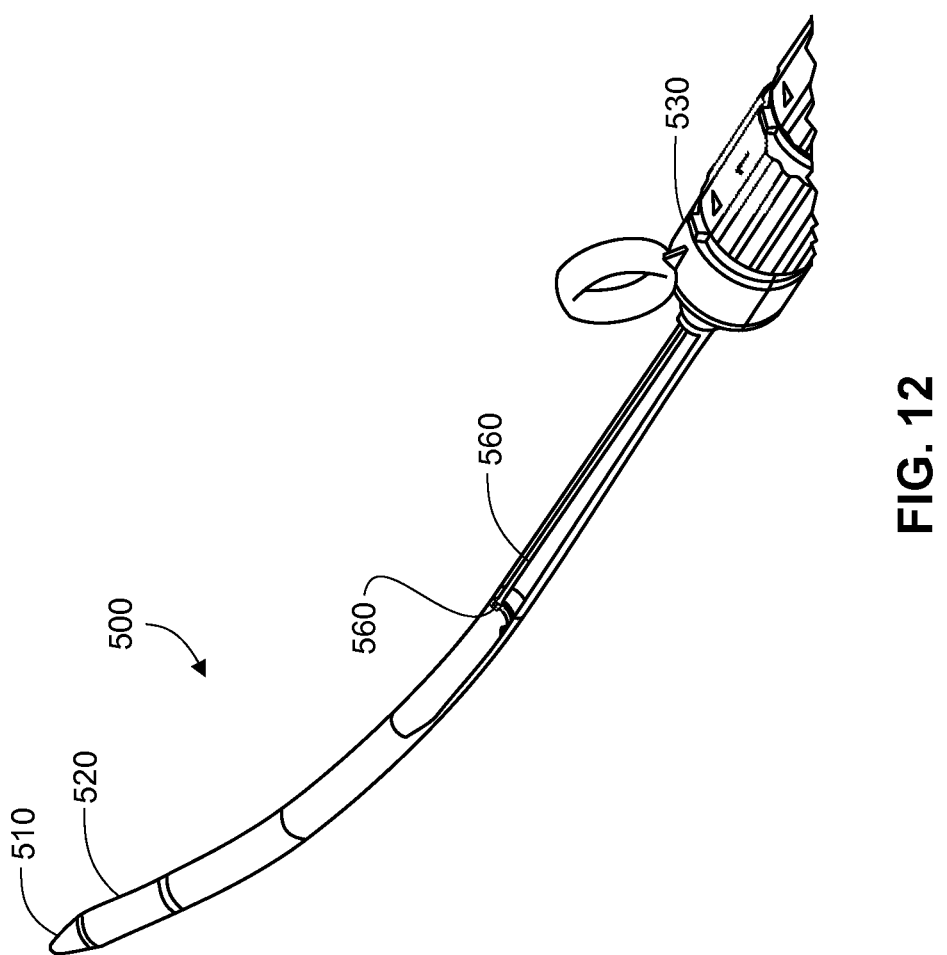

The flexibility of the second sheath is achieved by fabricating the second sheath using a metal support structure wherein the metal is one which will maintain a bent configuration after bending and in the absence of an external force. Accordingly, the second sheath can be bent to a particular angle prior to introduction of the delivery device into a patient or during delivery, and once bent, the second sheath maintains the bent angle (conformation) throughout delivery of the prosthetic valve and, optionally, during retrieval of the delivery device. A non-limiting example of such a metal is stainless steel. The metal support structure can be a braid of metal wires, a wire mesh and/or a coil of metal wires. The wires may or may not be flat. The thickness of the wire can vary as can the density of the wire braid, mesh or coil. In other words, the flexibility of the sheath will increase as the quantity of wire per unit area increases. For this embodiment, it is envisioned that any material can be used to construct second sheath 120, as long as that material allows second sheath 120 to be bent manually by the practitioner without assistance from other persons or tools. Alternatively, the practitioner may use a tool to bend second sheath 120 to a compatible bent configuration. In one embodiment, the implantation device is constructed to comprise a sheath configuration cable which can be used to bend the second sheath before or during the delivery procedure. In one embodiment, the sheath configuration cable is located within and through the lumen of the second sheath. The sheath configuration cable may be attached at or near its distal end to the second sheath, wherein this connection is located at or near the distal end of the second sheath. The proximal end of the configuration cable may be free, or may be connected to an element of the delivery device. In one embodiment, the proximal end of the configuration cable is attached to the control unit. In another embodiment, the proximal end of the configuration cable is attached to an independent configuration control lever. It is envisioned that once second sheath 120 is bent to a bent configuration, the bent configuration can be maintained at the same angle, ±1°, ±2°, ±3°, ±4°, or ±5° during the delivery procedure. An example of these embodiments is illustrated in FIGS. 11-12.

One example of a reversible connection between track wire 180 and leg member 160 of valve clasper 10 is shown in FIG. 3C. Prior to delivery and deployment of a valve prosthesis, the distal end of track wire 180 is threaded through leg member lumen 50 and bent back about 180 degrees. A track wire sheath 250 encases bent track wire 180 to maintain the connection of track wire 180 with leg member 160 until track wire sheath 250 is pulled proximal to unsheathe the bent portion of track wire 180 and allow track wire 180 to unbend and unthread through leg member lumen 50. A skilled artisan understands that many standard methods and devices may be used to reversibly connect a track wire to a valve clasper in such a way as to allow controlled release of the track wire from the valve clasper after deployment and implantation of the valve prosthesis.

Delivery device 100 further comprises a valve carrier as illustrated in FIGS. 3A and 3B. As referenced in FIGS. 3A, 3B and 4, valve carrier 270 is positioned in first sheath 110 prior to delivery of the valve prosthesis. Valve carrier 270 comprises a proximal disc member 275 and a distal disc member 274 with a central stem 276 connecting them. As shown in FIG. 3B, support frame 280 is positioned between proximal disc member 275 and distal disc member 274 when support frame 280 is in a compact condition within first sheath 110. The valve carrier functions to hold the support frame in its compact condition stationary within the first sheath during delivery of the valve prosthesis to the defective valve annulus. When the first sheath is move distal relative to the valve carrier, the support frame can expand radially to deploy within a valve annulus, at which time the valve carrier can be moved through the interior lumen of the deployed support frame and thereby removed from the patient's body with the delivery device.

Also shown in FIGS. 4-7 is control unit 260. Control unit 260 is designed to allow the user to individually control movements of different parts of the delivery device and valve prosthesis as described in the delivery method below. Accordingly, the first sheath, second sheath, valve clasper, track wire and valve carrier can each be controlled individually, which means that each can be moved in a proximal or distal direction independently of the other parts of the valve prosthesis and delivery device. Design and use of a control unit to individually control parts of a delivery such as that described herein are well known to the skilled artisan.

Methods for Delivery

Delivery device 100 can be advanced through a vessel or through the heart in the direction of blood flow to a valve annulus. The method of delivery using delivery device 100 is described here with reference to FIGS. 4-7.

In one embodiment, a trocar is inserted through the chest wall and the delivery device is advanced along a guide wire through and past the defective valve. Prior to delivery and when the delivery device is advanced to the defective valve, support frame 170 is in a compact condition and is fully encased within first sheath 110. Also encased by first sheath 110 is a valve carrier as described above and illustrated in FIGS. 3A and 3B. Valve clasper 140 is in a compact condition and fully encased within second sheath 120. Support frame 170 and valve clasper 140 are moveably attached, for example, by a suture loop as illustrated in FIGS. 1 and 2. Each leg member 160 of valve clasper 140 is reversibly connected at its distal end to a track wire 180, which in turn is attached at its proximal end to control unit 260. Delivery device 100 also comprises a track wire sheath (not shown) which encases track wire 180 as described above (see FIG. 3C).

Once first sheath 110 and second sheath 120 are advanced distal along a guide wire using a guide catheter 265 to or past the defective valve annulus such that u-shaped members 150 are also distal to the defective valve annulus, second sheath 120 is moved in a proximal direction independently of at least valve clasper 140, first sheath 110 and support frame 130. This uncovers u-shaped members 150 and allows them to expand radially as shown in FIG. 5.

At this time, first sheath 110 is moved independently of second sheath 120 in a proximal direction until the proximal end of support frame 170 is aligned with the proximal end of u-shaped members 150. Delivery device 100 is then moved in a proximal direction until u-shaped members 150 contact the commissure between each defective valve leaflet 285 and vessel wall 290 (see FIG. 6). In an alternative method, device 100 is pulled in a proximal direction until u-shaped members 150 contact the commissure between each defective valve leaflet 285 and vessel wall 290, at which time first sheath 110 is moved independently of second sheath 120 in a proximal direction until the proximal end of support frame 170 is aligned with the proximal end of u-shaped members 150.

Once u-shaped members 150 are aligned with support frame 130 and u-shaped members are seated within the commissure between each defective valve leaflet 285 and vessel wall 290 (see FIG. 6), first sheath 110 is moved independently of at least support frame 130, the valve carrier, and valve clasper 140 to allow support frame 130 to fully expand radially. The deployed support frame 130 is illustrated in FIG. 7. The valve carrier is not shown in this illustration. Note that track wires 180 are still connected to valve clasper 140 and control unit 260.

Control unit 260 is manipulated to cause release of track wires 180, for example, as described above. Delivery device 100 can now be moved in a proximal direction to remove the device from the patient. In one embodiment, second sheath 120 is moved independently in a distal direction until it is approximate adjacent to first sheath 110 prior to removal of delivery device 100.

III. A Surgical Delivery Device for Catheter-Based Delivery of a Cardiac Valve Prosthesis Described herein is a sutureless valve prosthesis delivery device suitable for percutaneous delivery of a valve prosthesis to repair a damaged cardiac valve. This device is especially useful for repairing an aortic valve, a pulmonary valve, a mitral valve, or tricuspid valve. In this aspect, the expandable support frame to which the prosthetic valve leaflets are attached is encased for delivery in a tubing with flexibility that allows the device to easily navigate the vessels leading to the cardiac valves from an access point relatively close to the defective cardiac valve, while causing minimal or no damage to the vessel walls.

It is envisioned that his device is particularly useful with a surgical procedure in which an incision is made in a vessel close to the heart. These vessels, such as the aorta, carotid artery, subclavian artery, innominate artery, the superior vena cava, and the pulmonary artery and veins have a relatively large diameter, for example, a diameter larger than that of the femoral artery, a popular route of percutaneous delivery of valve prostheses. Accordingly this device provides improvements in the delivery and implantation of sutureless valve prostheses by, for example, reducing damage to the interior wall of vessels through which a delivery device is advanced.

An implantation device comprising a delivery device for retrograde delivery of a cardiac valve prosthesis is described below. The implantation device comprises the delivery device and a valve prosthesis. The delivery device has an outer sheath for passing through a vessel or through chamber walls. The sheath may be comprised of a polymeric material or of a polymeric and metallic material (e.g., braiding or coiled to provide additional strength, kink resistance, etc.) The delivery sheath can be retracted to release the valve clasper and valve frame of the valve prosthesis.

Figure 9:
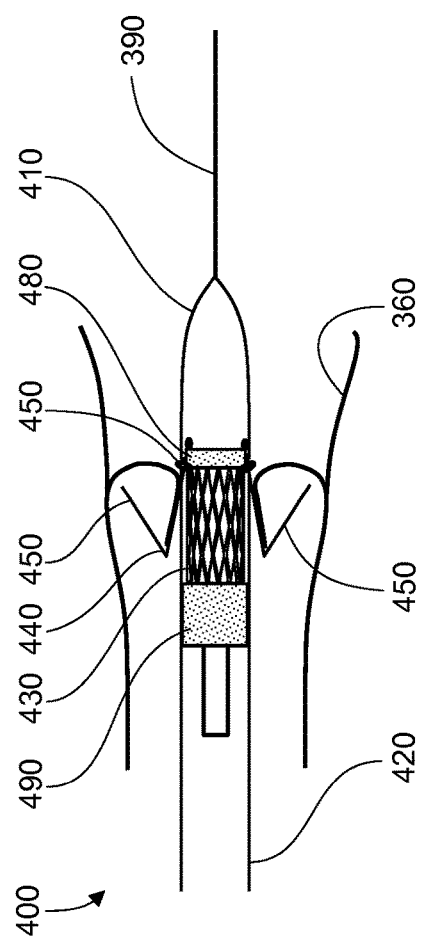
Figure 10:
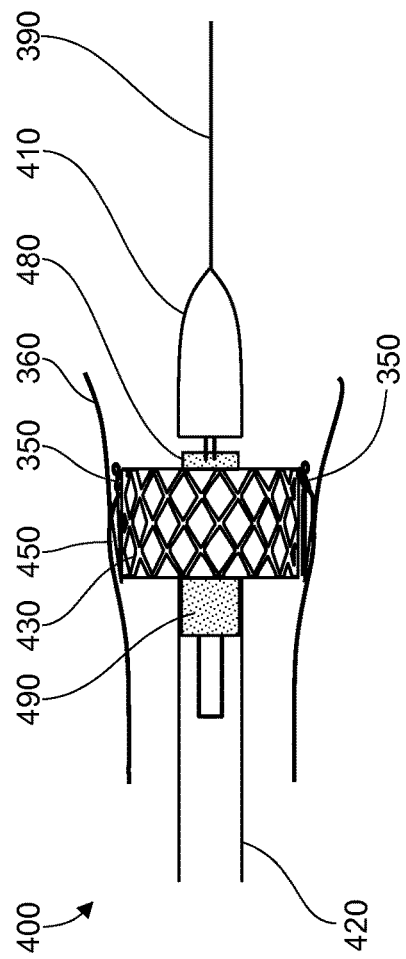

Configuration of this device during delivery to a defective valve and after deployment of the support frame is illustrated in FIGS. 8-10. A delivery device 400, comprises a first sheath 410, which is distal to a second sheath 420, which is distal to a control unit (not illustrated in FIGS. 8-10), and a valve prosthesis as described above in which a support frame comprising prosthetic valve leaflets is moveably connected to a valve clasper. The distal tip of the delivery device may have an angle for more aligned placement in the native anatomy. The angle may be from about 1 degree to 45 degrees, or 5 degrees to 30 degrees.

In FIG. 10, a suture loop 350 is depicted. As described above, there is a suture loop for each leg member of the valve clasper to provide movable attachment to the support frame. Prior to delivery, both a support frame 430 and the proximal part of a valve clasper 440 (including u-shaped members 450) are in a compact condition within second sheath 420. Delivery device 400 further comprises a locking member 480 which is positioned within first sheath 410 (nose cone). A portion of each of the distal ends of each of valve clasper leg members 460 is positioned within first sheath 410 between locking member 480 and the internal surface of first sheath 410. Locking member 480 may be fabricated from a shape memory material such as nitinol such that it provides the radial force needed to secure the proximal ends of clasper leg members 460 within first sheath 410. Delivery device 400 may further comprise a stabilizing member 490 which can function as a counter force to maintain the position of support frame 430 within second sheath 420 in a compact position as support frame 430 is optimally aligned with valve clasper 440 prior to deployment of support frame 430.

Second sheath 420 is comprised of material which allows second sheath 420 to have flexibility and strength appropriate to provide delivery of a valve prosthesis to a cardiac valve while causing no or minimal damage to a vessel through which the delivery device travels. In one embodiment, second sheath 420 may comprise a plastic or polymer and metal wires which may be braided or configured in such a way as to provide sufficient flexibility or manufactured using other methods known to the ordinarily skilled artisan and as discussed in further detail above. In another embodiment, second sheath 420 is fabricated as described in U.S. Application Pub. No. 2010/0274088, the contents of which are incorporated herein by reference in their entirety.

Figure 13:
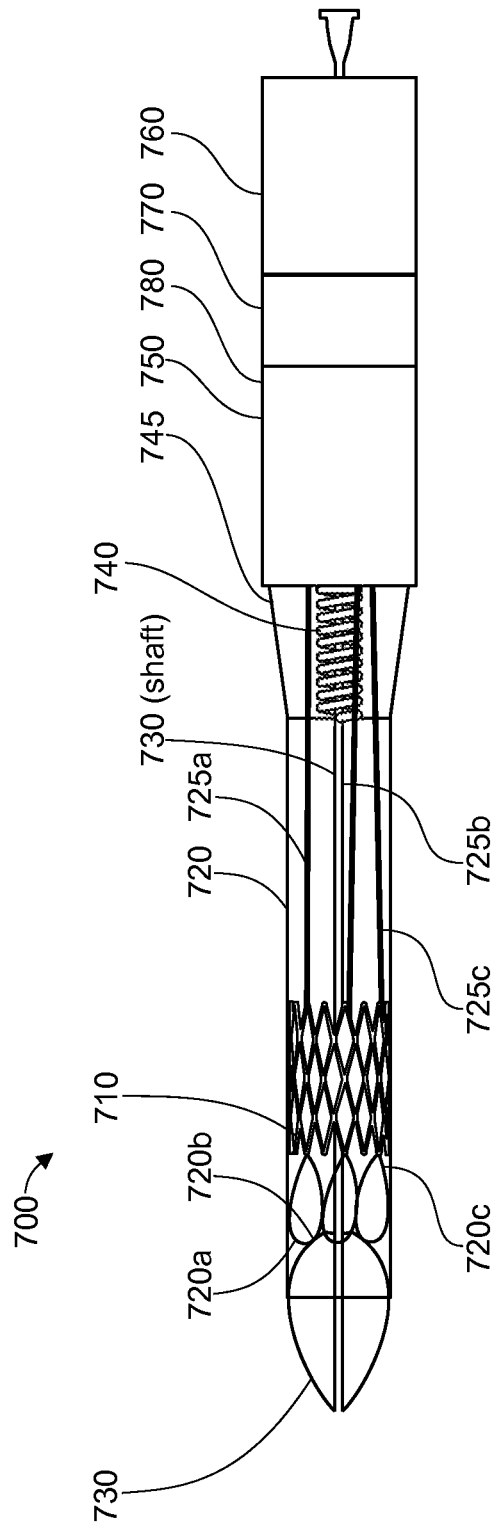
FIG. 13 illustrates an embodiment of a sutureless valve prosthesis implantation device comprising a spring mechanism.

An example of the flexibility of a second sheath is illustrated in FIGS. 11-12. FIGS. 11 and 12 show an embodiment of a implantation device 500 having a first sheath 510, a second sheath 520 and a control unit 530. FIG. 11 illustrates two conformations of second sheath 520 which is shown as 520a in a first bent conformation and as 520b as a second bent conformation. In one embodiment, the bending of second sheath 520 is controlled through a bend configuration element 540 which is attached to the proximal end of a sheath configuration cable which is attached to second sheath 520. This is further illustrated in FIG. 12, which shows a sheath configuration cable 550 which is located in the lumen of second sheath 520. The distal end of sheath configuration cable 550 is attached to the inner surface of second sheath 520 at or near the distal end of second sheath 520. The proximal end of sheath configuration cable 550 may be free or may be attached to a moveable element of control unit 530 which allows control of sheath configuration cable 550. For example, pulling on bend configuration element 540 and/or on sheath configuration cable 550 will bend second sheath 520. Another embodiment of an implantation device is illustrated in FIG. 13. FIG. 13 show an exemplary embodiment of an implantation device 700 wherein a valve prosthesis and valve claspers as described above are fully or partially encased in a first sheath prior to inserting the implantation device into a patient. As shown in FIG. 13, valve prosthesis 710 and valve claspers 720a, 720b, and 720c, are fully encased in a first sheath 720. In this embodiment, u-shaped members of valve claspers 720abc are located distal to valve prosthesis 710. The u-shaped members may be fully or partially covered by the first sheath. In some embodiments, the valve prosthesis is fully encased by the first sheath. FIG. 13 illustrates an embodiment of the control unit, shown here as control unit 750. In this embodiment, control unit 750, comprises a spring control element (shown as auto control element 745), a sheath control element (shown as sheath control element 780), a release knob (shown as release knob 770), and a handle (shown as handle 760). The implantation device also comprises a second sheath which may also be referred to as a nose cone. The diameter of the second sheath decreases towards the distal end of the second sheath relative to the central portion of the second sheath (providing the second sheath with the shape of a nose cone). The diameter of the second sheath may also decrease towards the proximal end of the second sheath relative to the central portion of the second sheath, allowing the proximal end of the second sheath to be encased or covered by the first sheath prior to, during and after delivery of the valve prosthesis. This feature of the proximal end of the second sheath is advantageous in part because it will reduce or prevent damage that may be caused to the vessel walls or surrounding tissue by the proximal end of a nose cone during delivery of the valve prosthesis and/or during retrieval of the implantation device from the patient. A particular embodiment of the second sheath as described here is shown in FIG. 13 as second sheath 730. The second sheath can be solid with a central lumen, or can be hollow. The second sheath will have an aperture or opening at its proximal and distal ends. A second sheath shaft can be attached to the second sheath. The second sheath shaft may be fabricated as part of the second sheath or the distal end of the second sheath shaft may be attached to a central portion of the second sheath. An embodiment of the second sheath shaft is illustrated in FIG. 13 as second sheath shaft 730.

The implantation device, such as that shown in FIG. 13 and described above, further comprises one or more track wires. The distal end of each of the one or more track wires is attached to each of the support frame. In one embodiment, the distal end of each of the one or more track wires is attached to the proximal end of the support frame. An embodiment of the plurality of track wires is shown in FIG. 13 as 725a, 725b, and 725c.

In one embodiment, the implantation device further comprises a spring mechanism comprising a spring, wherein a spring is attached to the proximal end of the second sheath and to a first sheath control element within the control unit. The first sheath control element is used to control distal and proximal movement of the first sheath, wherein the first sheath encases the valve prosthesis and may fully or partially encase the valve claspers. Prior to implantation, the spring is in a partially or fully compressed condition. When the distal end of the implantation device is forwarded toward the defective valve annulus, once the distal end of the implantation device is near, within or through the defective valve annulus, the first sheath control element is manipulated (for example, rotated, or moved right/left or up/down) to cause movement of the first sheath in a direction to partially or fully uncover the claspers. As the first sheath control element is manipulated, the proximal end of the second sheath, connected to the spring via the second sheath shaft, maintains proximity to the distal end of the first sheath, wherein the proximal end of the second sheath remains within about 2 mm, 3 mm, 4 mm, 5 mm, 6 mm, 7 mm, 8 mm 9 mm, 1 cm, 1.5 cm of the distal end of the first sheath. In some embodiments, the relatively narrow proximal end of the second sheath may be within the lumen of the distal end of the first sheath. The first sheath control element is manipulated until a hard stop is encountered, wherein the proximal end of the second sheath is no longer held in proximity to the distal end of the first sheath (wherein the proximal end of the second sheath is no longer maintained at a distance no more than about 2 mm, 3 mm, 4 mm, 5 mm, 6 mm, 7 mm, 8 mm 9 mm, 1 cm, 1.5 cm away from the distal end of the first sheath). The hard stop is encountered only with respect to the spring and second sheath. When this hard stop is encountered, the u-shaped members of the valve claspers are at least partially or are fully uncovered by the first sheath. The first sheath is still movable in both a distal and proximal direction through manipulation of the first sheath control element.

Once this hard stop is encountered, the first sheath control element can be manipulated further to move the first sheath in the proximal direction. Accordingly, after at least the u-shaped members of the valve claspers are no longer covered by the first sheath and have expanded radially, the implantation device is moved toward the direction of the defective valve annulus as described above until each of the valve claspers are properly positioned within the defective valve annulus. Once the valve claspers are properly positioned within the defective valve annulus, the first sheath control element is manipulated to move the first sheath in a proximal direction to uncover the support frame of the valve prosthesis to deploy the valve prosthesis in the native valve annulus as described above, wherein the native valve leaflets become compressed between the expanded support frame and the valve claspers.

A particular embodiment of this implantation device comprising the spring mechanism is shown in FIG. 13. A second sheath 730 is present at the distal end of implantation device 700. In this embodiment, second sheath 730 is shaped such that the diameter at the distal and proximal ends of second sheath 730 is smaller than the diameter of the middle of second sheath 730. Furthermore, the proximal end of second sheath 730 is at least partially encased by first sheath 720. First sheath 720 fully encases a valve prosthesis 710 and a plurality of valve claspers 720a, b, c). Each of valve claspers 720a,b,c is connected to the support frame of valve prosthesis 710 by suture, fabric, or flexible member. The proximal end of each of release cable 725a, b, c is attached directly or indirectly to a release control element 770 which is part of a control unit 750. Control unit 750 can be configured in various ways as understood by a person having ordinary skill in the art and FIG. 13 is in no way limiting to a particular configuration. Control unit 750 provides an example of an implantation device control unit which have control elements for independent or concerted manipulation of parts of the valve prosthesis delivery device including, but not limited to the first and second sheaths, the valve prosthesis, the track wires, and the spring when present. FIG. 13 also illustrates an embodiment wherein control unit 750 comprises a second sheath auto control element 745. Auto control element 745 encases at least a portion of a spring 740 wherein the spring is attached at its distal end to a second sheath shaft 730 and at its proximal end to auto control element 745. A first sheath control element 780 as shown in FIG. 13 can be manipulated to control the proximal and distal movement of first sheath 720, and as described above, will result in a partial extension of spring 740 which in turn allows second sheath 730 to stay in proximity of the distal end of first sheath 720 as described above. In the embodiment illustrated in FIG. 13, rotation of first sheath control element 780 will result in a hard stop wherein spring 740 is no longer extended and further rotation of first sheath control element 780 to move first sheath 720 in a proximal direction to uncover valve prosthesis 710 will result in first sheath 720 moving independently of second sheath 730. Once valve prosthesis 710 is fully uncovered and deployed, release knob 770 can be manipulated to release track wires 790a,b,c from valve claspers 720a,b,c and first sheath control element 780 can be rotated in the opposite direction to bring the proximal end of second sheath 730 within proximity of the distal end of first sheath 720. Implantation device 700 can then be removed from the patient, doing none or minimal damage to vessel walls or tissue of the patient.

Methods for Delivery

Delivery device 400 is designed to allow delivery of a valve prosthesis in a retrograde fashion, or opposite the direction of blood flow through the defective valve. A method for delivery using an implantation device comprising delivery device 400 and a movably attached valve prosthesis as described above is described here with reference to FIGS. 8-10. The distal end of the delivery device is advanced along a guide wire in part by using a guide catheter 390, until first sheath 410 is approximately within the defective valve annulus and second sheath 420 is proximal to native valve leaflets 370. Second sheath 420 is then moved in a proximal direction while valve clasper 440 is held stationary along the longitudinal axis. As u-shaped members 450 of valve clasper 440 are uncovered, u-shaped members 450 expand radially.

At this time, second sheath 420 is moved in a distal direction while valve clasper 440 is held stationary along the longitudinal axis. This movement of second sheath 420 functions to align support frame 430 with valve clasper 440, thereby properly aligning support frame 430 and its associated prosthetic valve leaflets within the valve annulus. Importantly, support frame 430 moves along the longitudinal axis relative to valve clasper 440 in order to become concentric with valve clasper 440. This motion is allowed in part by the movably connected aspect of the valve prosthesis, which in turn is provided in this particular example by suture loops 350. As support frame 430 is moved in a distal direction, suture loops 350 slide along the leg members of valve clasper 440 as described above. Delivery device 400 is then moved in a distal direction until u-shaped members 450 contact the commissure between each defective valve leaflet 370 and vessel wall 360.

In an alternative method, after u-shaped members 450 are uncovered and expand radially, device 400 is advanced in a distal direction until u-shaped members 450 contact the commissure between each defective valve leaflet 370 and vessel wall 360, at which time second sheath 420 is moved independently of first sheath 410 in a distal direction until the distal end of support frame 430 is aligned with u-shaped members 450, thereby properly aligning support frame 430 with the native valve annulus.

The advancing the second sheath 420 in a distal direction, wherein valve clasper 440 is held stationary results in release of locking member 480 from first sheath 410. As a result, leg members of valve clasper 440 are no longer locked within first sheath 410 and can thereby accommodate the later radial expansion of support frame 430.

Once u-shaped members 450 are properly aligned with support frame 430 and u-shaped members are seated within the commissure between each defective valve leaflet 370 and vessel wall 360 (see FIG. 9), first sheath 410 is moved in a proximal direction along the longitudinal axis independently of at least support frame 430 and valve clasper 440 to allow support frame 430 to fully expand radially. The deployed support frame 430 is illustrated in FIG. 10. Full deployment of support frame 430 results in a sandwiching of native valve leaflets 370 between u-shaped members 450 and support frame 430, thereby securing the valve prosthesis in a proper and functional position within the native cardiac valve annulus. At this time, delivery device 400 is removed from the patient.

The implantation device described here comprises a control unit (not depicted in FIGS. 8-10). The control unit is designed and manufactured according to methods commonly available to the skilled artisan and functions to independently control at least the first sheath, second sheath, valve clasper, support frame, locking member, and stabilizing member.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A delivery device for delivering a heart valve prosthesis, the delivery device comprising:
   a first sheath configured to encase at least a portion of an expandable support frame of the heart valve prosthesis;
   a second sheath configured to encase a valve clasper of the heart valve prosthesis, the valve clasper being coupled to the expandable support frame; and
   a control unit operably coupled to the first and second sheaths,
   wherein along a longitudinal axis, the first sheath is distal to the second sheath, and the second sheath is distal to the control unit, and
   wherein the second sheath comprises a bent configuration in which (i) the second sheath has an angle of between about 5 degrees to 60 degrees and (ii) the second sheath maintains the bent configuration, at the same angle ±5 degrees in the absence of a force applied thereto, during delivery of the heart valve prosthesis and removal of the delivery device.

2. The delivery device of claim 1, further comprising a valve carrier which is encased by the first sheath.

3. The delivery device of claim 1, further comprising a heart valve prosthesis carried by the delivery device.

4. The delivery device of claim 1, wherein the first sheath and the second sheath are separable relative to each other along the longitudinal axis to permit expansion and release of the support frame or the valve clasper.

5. The delivery device of claim 1, further comprising a locking member comprising a shape memory material configured to provide a radial outward force against the valve clasper.

6. The delivery device of claim 1, wherein the angle is between about 20 degrees to 40 degrees.

7. The delivery device of claim 1, wherein the angle is between about 10 degrees to 60 degrees.

8. The delivery device of claim 1, wherein the first sheath encases at least a portion of at least one u-shaped member of a valve clasper.

9. The delivery device of claim 1, wherein the first sheath is configured to extend along and encase an entirety of the support frame in a collapsed configuration.

10. The delivery device of claim 1, wherein the valve clasper is coupled to the expandable support frame via a suture.

11. A method for delivering a prosthetic heart valve to an implantation site of a patient, the method comprising:
   introducing a valve delivery device into the implantation site, wherein the valve delivery device comprises:
      a first sheath encasing at least a portion of an expandable support frame of the prosthetic heart valve;
      a second sheath encasing a valve clasper of the prosthetic heart valve, the valve clasper being coupled to the expandable support frame and comprising three u-shaped members and three leg members;
      a control unit operably coupled to the first and second sheaths; and
      three track wires providing an operable connection between the three leg members and the control unit, each of the three track wires being reversibly attached to each of the three leg members;
   wherein along a longitudinal axis, the first sheath is distal to the second sheath, and the second sheath is distal to the control unit, and
   wherein the second sheath comprises a bent configuration in which the second sheath has an angle of between about 5 degrees to 60 degrees;

advancing a distal end of the valve delivery device to a defective cardiac valve until the three u-shaped members are located adjacent to an annulus of the defective cardiac valve;

proximally retracting the second sheath relative to the valve clasper to uncover the three u-shaped members;

moving the delivery device relative to the annulus to seat the three u-shaped members against the annulus;

moving the first sheath relative to the support frame to uncover the expandable support frame;

detaching each of the three track wires from the three leg members;

removing the valve delivery device from the patient; and maintaining the bent configuration of the second sheath, at the same angle ±5 degrees in the absence of a force applied to the second sheath, during delivery of the prosthetic heart valve and removal of the valve delivery device.

12. The method of claim 11, wherein the first sheath encases a valve carrier which holds the support frame stationary within the first sheath prior to deployment of the support frame.

13. The method of claim 11, wherein the advancing comprises advancing the valve delivery device in a direction of blood flow.

14. The method of claim 11, wherein the advancing comprises advancing the valve delivery device in a direction opposite of blood flow.

15. The method of claim 11, wherein the defective cardiac valve is an aortic valve.

16. A delivery device for delivering a heart valve prosthesis, the delivery device comprising:

a first sheath configured to encase at least a valve clasper;

a second sheath configured to encase at least a portion of an expandable support frame, the valve clasper being coupled to the expandable support frame; and a control unit operably coupled to the first and second sheaths, wherein along a longitudinal axis, the first sheath is distal to the second sheath, and the second sheath is distal to the control unit, and wherein the second sheath comprises a bent configuration in which (i) the second sheath has an angle of between about 5 degrees to 60 degrees and (ii) the second sheath maintains the bent configuration, at the same angle ±5 degrees in the absence of a force applied thereto, during delivery of the heart valve prosthesis and removal of the delivery device.

17. The delivery device of claim 16, further comprising a locking member that comprises a shape memory material configured to provide a radial outward force against the valve clasper within the first sheath.

18. The delivery device of claim 16, wherein the angle is between about 20 degrees to 40 degrees.

19. The delivery device of claim 16, wherein the first sheath and the second sheath are separable relative to each other along the longitudinal axis to permit expansion and release of the support frame or the valve clasper.

20. The delivery device of claim 16, wherein the angle is between about 10 degrees to 60 degrees.

21. The delivery device of claim 16, wherein the valve clasper is coupled to the expandable support frame via a suture.

22. A method for deploying a prosthetic valve to an implantation site of a patient, the method comprising:

introducing a valve delivery device into a vessel of a patient, wherein the valve delivery device comprises:

a first sheath encasing at least a portion of a valve clasper;

a second sheath encasing at least a portion of an expandable support frame, the valve clasper being coupled to the expandable support frame; and a control unit operably coupled to the first and second sheaths, wherein along a longitudinal axis, the first sheath is distal to the second sheath, and the second sheath is distal to the control unit, and wherein the second sheath comprises a bent configuration in which the second sheath has an angle of about 5 degrees to 60 degrees;

advancing the valve delivery device through the vessel toward a defective native valve until the first sheath is adjacent to an annulus of the defective native valve;

moving the first sheath relative to the valve clasper along the longitudinal axis to permit the valve clasper to expand radially;

moving the second sheath relative to the valve clasper along the longitudinal axis until the expandable support frame is aligned with the valve clasper;

moving the delivery device in a distal direction until the valve clasper is in contact with a sinus of the defective native valve;

proximally retracting the second sheath relative to the expandable support frame and valve clasper along the longitudinal axis until the expandable support frame expands; and maintaining the bent configuration of the second sheath, at the same angle ±5 degrees in the absence of a force applied to the second sheath, during delivery of the prosthetic valve and removal of the valve delivery device.

23. The method of claim 22, wherein the vessel is an aorta, superior vena cava or a pulmonary vein or artery.

24. The method of claim 22, wherein the advancing comprises advancing the valve delivery device in a direction of blood flow.

25. The method of claim 22, wherein the advancing comprises advancing the valve delivery device in a direction opposite of blood flow.

26. The method of claim 22, wherein the defective native valve is an aortic valve.

* * * * *